United States Patent [19]
Bang et al.

[11] Patent Number: 5,591,766
[45] Date of Patent: Jan. 7, 1997

[54] SOLID ORAL FORMULATIONS OF PYRIDONE CARBOXYLIC ACIDS

[75] Inventors: Won Y. Bang, Sungnam; Kyu J. Yeon, Seoul; Yeong O. Baik, Soowun; Young H. Kim, Seoul; Kwan H. Park, Kyunggi; Ki H. Lee, Soowun; Jin W. Kim, Sungnam, all of Rep. of Korea

[73] Assignee: Cheil Foods & Chemicals, Inc., Seoul, Rep. of Korea

[21] Appl. No.: 332,780

[22] Filed: Nov. 1, 1994

Related U.S. Application Data

[63] Continuation-in-part of Ser. No. 160,821, Dec. 3, 1993, Pat. No. 5,527,910.

[30] Foreign Application Priority Data

Jul. 18, 1994 [KR] Rep. of Korea .................. 94-17460

[51] Int. Cl.⁶ ......................................... A61K 31/40
[52] U.S. Cl. ............................................... 514/412
[58] Field of Search ................................. 514/412

[56] References Cited

U.S. PATENT DOCUMENTS 4,988,709  1/1991  Ogata et al. ..................... 514/314

FOREIGN PATENT DOCUMENTS 0413455   2/1991  European Pat. Off. .
64-56673  3/1989  Japan .

*Primary Examiner*—Zohreh Fay
*Attorney, Agent, or Firm*—Burns, Doane, Swecker & Mathis, L.L.P.

[57] ABSTRACT

A solid oral pharmaceutical formulations of novel pyridone carboxylic acid compounds and esters or salts thereof having powerful antibacterial activities is disclosed.

4 Claims, No Drawings

SOLID ORAL FORMULATIONS OF PYRIDONE CARBOXYLIC ACIDS

This application is a continuation-in-part of U.S. Ser. No. 08/160,821, filed Dec. 3, 1993, now U.S. Pat. No. 5,527,910.

FIELD OF THE INVENTION

The invention relates to solid oral pharmaceutical formulations of novel pyridone carboxylic acid compounds and esters or salts thereof having powerful antibacterial activities.

BACKGROUND OF THE INVENTION

A number of quinolone compounds have been developed and proven successful in commerce, attributed to their potent and broad spectrum of antibacterial activities. Included among such quinolone compounds are Norfloxacine, Enoxacine, Ofloxacine, Ciprofloxacine and the like.

In recent years, extensive investigation has been made to develop a novel structure of pyridone carboxylic acid derivatives which have more potent and broad antibacterial activities. Most of such investigation has been into the development of new substituents at 7-position of the quinolone nucleus. As prior art references which disclose such derivatives, U.S. Pat. No. 4,988,709, European Patent 0413 455 and Japanese Unexamined Patent Publication 89-56673 may be mentioned.

We have found another class of novel compounds of formula(I) which is claimed in pending U.S. Ser. No. 08/160821 filed Dec. 3, 1993. As the compounds of formula (I) as represented below were in vitro evaluated about their efficacy, it was found that these compounds, especially 1-cyclopropyl-6-fluoro-1,4-dihydro-4-oxo-7-([1α,5α,6β]6-amino-1-methyl-3-azabicyclo[3.2.0]heptan-3-yl)-1,8-naphtyridine-3-carboxylic acid (hereinafter "compound A") exhibit superior antibacterial activities to Lomefiroxacin and Ofiofloxacine which are utilized for-combating gram-negative and gram-positive bacteria and that these compounds including compound A has 2 to 16 times as much antibacterial activity as Ciprofloxacin, especially against gram-positive bacteria. Moreover, the compounds of formula(I) as represented above, especially compound A, show better bioavailability and half-life than drugs of quinolone compounds which either are commercially available or still in development.

We have conducted much investigation in developing advantageous ways for orally administrating the compounds of formula(I). Therefore, it is the object of the present invention to provide the pharmaceutical formulations of the formula(I) compounds to be orally administrated.

SUMMARY OF THE INVENTION

The present invention is directed to the solid pharmaceutical formulations for oral administration which comprise 30.0–95.0% by weight of at least one of pyridone carboxylic acid compounds of the following formula:

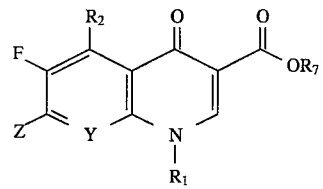

wherein $R_1$ represents a lower alkyl, a halogen-substituted lower alkyl, a lower alkenyl, a cycloalkyl or a substituted or unsubstituted phenyl; $R_2$ represents a hydrogen atom, a lower alkyl or an amino group; Y represents a nitrogen atom or the group C—X in which X is a hydrogen, a halogen or an alkoxy group; $R_7$ represents a hydrogen or a lower alkyl group; and Z is a group having the following formula:

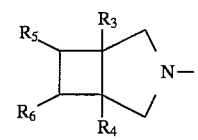

in which each of $R_3$ and $R_4$ represent independently a hydrogen or a lower alkyl group, with the proviso that one of $R_3$ and $R_4$ is a lower alkyl group; one of $R_5$ and $R_6$ is a hydrogen and another is a hydroxy, a lower alkoxy, or an amino group which is unsubstituted or substituted by a lower alkoxy or a lower alkyl group; and esters or salts thereof with combination of 2.0–10.0% by weight of dry binder cellulose and/or wet binder povidone, 0.0–35.0% by weight of disintegrating agent starch, 2.0–20.0% by weight of co-binder saccharide, 0.0–2.0% by of weight of fluid-enforcing agent and 0.0–3.0% by weight of lubricating agent.

In terms of bioavailability and shelf life, the pharmaceutical formulations according to the invention are substantially superior to the corresponding formulations produced according to common methods in pharmacy.

DISCLOSURE OF THE PREFERRED EMBODIMENT

In a preferred aspect, the pharmaceutical formulations according to the invention comprise 60.0–90.0 wt % of formula(I) compounds, 2.5–6.0 wt % of dry binder cellulose and/or wet binder povidone, 10.0–18.0 wt % of disintegrating agent starch, 4.0–10.0 wt % of co-binder saccharide, 0.5–1.0 wt % of fluid-enforcing agent and 0.5–2.0 wt % of lubricating agent.

In a particularly preferred aspect, the pharmaceutical formulations according to the invention comprise 71.3–79.1 wt % of compound A, 2.8–3.7 wt % of polyvinylpyrrolidone, 8.4–9.2 wt % of sodium starch glycolate(Premogel), 6.6–8.7 wt % of lactose, 0.6–0.8 wt % of hard anhydrous silicic acid and 1.3–1.8 wt % of magnesium stearate.

A suitable binder is polyvinylpyrrolidone having 30,000–50,000 molecular weight, 20–601 μm particle size and up to 5.0% water content.

A disintegrating agent which may be suitably used is a common type of starch. Preferred is corn starch, especially sodium starch glycolate (Premosel).

A fluid-enforcing agent which would be used as powdered base is a particulate substance whose property is capable of imparting both increased fluidity and exudation to sticky particulates. A suitable fluid-enforcing agent includes Aerosil [highly pure amorphous silicon dioxide with (>99.8%

SiO)], Aerosil972 (pure silicon dioxide with hydrophobic property due to a chemically changed methyl group).

An example of lubricating agent includes talc, calcium stearate, magnesium stearate and solid polypropyleneglycol. Suitable is magnesium stearate.

The solid oral pharmaceutical formulations according to the invention are made by mixing 30.0–95.0 wt % of compound A with 2.0–10.0 wt % of dry binder cellulose and/or wet binder povidone, if necessary up to 35.0 wt % of disintegrating agent starch, if necessary 2.0–20.0 wt % of co-binder saccharide, if necessary up to 2.0 wt % of fluid-enforcing agent, and if necessary up to 3.0 wt % of lubricating agent, and drying, pressing, disrupting and screening the resulting mixture. If necessary, the mixture is compressed into a tablet or filled into a capsule. One variation of the aforementioned method comprises granulating compound A in a fluidized-bed granulator, with the compound A being continuosly nebulized with water or binder solution and simultaneously being allowed to warm to a dryness, screening the resulting granules and, if necessary compressing the granules into a tablet. In alternative variation, compound A is granulated with dry binder cellulose, if necessary in the presence of disintegrating agent starch and/or with wet binder povidone, disintegrating agent starch and co-binder saccharide, the resulting granules are screened, and if necessary mixed with the other additives and compressed into a tablet or filled in a capsule.

Advantageously, granules with diameter between 0.8 and 2 mm are screened and compressed into a tablet or filled in a capsule. It is also preferred that compound A is mixed with corn starch, Avicel® and Aerosil®, the mixture is granulated, mixed with magnesium stearate and compressed into a tablet.

The preparative formulations according to the invention may further contain colorant, flavoring agent, sweetner, preservative and the like.

EXAMPLE 1

| ingredients | per tablet |
|---|---|
| Compound A (200 mg as free base) | 219.6 mg |
| Povidone(PVP-K30) | 9.0 mg |
| Sodium starch glycolate (Premogel) | 28.0 mg |
| Galactose | 17.3 mg |
| Hard anhydrous silicic acid | 2.0 mg |
| Magnesium stearate | 4.1 mg |
| Uncoated tablet | 280.0 mg |
| Lacquer shell: hydroxypropyl cellulose | 3.0 mg |
| PEG 4000 | 1.0 mg |
| Titanic dioxide | 1.0 mg |
| Coated tablet | 285.0 mg |

EXAMPLE 2

| ingredients | per tablet |
|---|---|
| Compound A (300 mg as free base) | 329.4 mg |
| Povidone(PVP-K30) | 13.4 mg |
| Sodium starch glycolate (Premogel) | 42.0 mg |
| Galactose | 26.1 mg |
| Hard anhydrous silicic acid | 2.8 mg |
| Magnesium stearate | 6.3 mg |
| Uncoated tablet | 420.0 mg |
| Lacquer shell: hydroxypropyl cellulose | 3.9 mg |
| PEG 4000 | 1.3 mg |
| Titanic dioxide | 1.3 mg |
| Coated tablet | 426.5 mg |

EXAMPLE 3

| ingredients | per tablet |
|---|---|
| Compound A (400 mg as free base) | 439.2 mg |
| Povidone(PVP-K30) | 17.9 mg |
| Sodium starch glycolate (Premogel) | 56.0 mg |
| Galactose | 34.7 mg |
| Hard anhydrous silicic acid | 3.8 mg |
| Magnesium stearate | 8.4 mg |
| Uncoated tablet | 560.0 mg |
| Lacquer shell: hydroxypropyl cellulose | 4.4 mg |
| PEG 4000 | 1.8 mg |
| Titanic dioxide | 1.8 mg |
| Coated tablet | 568.0 mg |

EXAMPLE 4

| ingredients | per tablet |
|---|---|
| Compound A (600 mg as free base) | 658.7 mg |
| Povidone(PVP-K30) | 26.9 mg |
| Sodium starch glycolate (Premogel) | 84.0 mg |
| Galactose | 52.0 mg |
| Hard anhydrous silicic acid | 5.8 mg |
| Magnesium stearate | 12.6 mg |
| Uncoated tablet | 840.0 mg |
| Lacquer shell: hydroxypropyl cellulose | 6.2 mg |
| PEG 4000 | 1.8 mg |
| Titanic dioxide | 2.0 mg |
| Coated tablet | 850.0 mg |

EXAMPLE 5

| ingredients | per tablet |
|---|---|
| Compound A (500 mg as free base) | 548.9 mg |
| Povidone(PVP-K30) | 22.4 mg |
| Sodium starch glycolate (Premogel) | 70.0 mg |
| Galactose | 43.4 mg |
| Hard anhydrous silicic acid | 4.8 mg |
| Magnesium stearate | 10.5 mg |
| Uncoated tablet | 700.0 mg |
| Lacquer shell: hydroxypropyl cellulose | 6.2 mg |
| PEG 4000 | 1.8 mg |
| Titanic dioxide | 2.0 mg |
| Coated tablet | 710.0 mg |

EXAMPLE 6

| ingredients | per tablet |
|---|---|
| Compound A (750 mg as free base) | 823.4 mg |
| Povidone(PVP-K30) | 33.6 mg |
| Sodium starch glycolate (Premogel) | 105.0 mg |
| Galactose | 65.0 mg |
| Hard anhydrous silicic acid | 7.3 mg |
| Magnesium stearate | 15.7 mg |

-continued

| ingredients | per tablet |
| --- | --- |
| Uncoated tablet | 1050.0 mg |
| Lacquer shell: hydroxypropyl cellulose | 8.2 mg |
| PEG 4000 | 2.4 mg |
| Titanic dioxide | 2.4 mg |
| Coated tablet | 1063.0 mg |

EXAMPLE 7

| ingredients | per tablet |
| --- | --- |
| Compound A (100 mg as free base) | 109.8 mg |
| Povidone(PVP-K30) | 4.5 mg |
| Sodium starch glycolate (Premogel) | 14.0 mg |
| Galactose | 8.7 mg |
| Hard anhydrous silicic acid | 1.0 mg |
| Magnesium stearate | 2.0 mg |
| Uncoated tablet | 140.0 mg |
| Lacquer shell: hydroxypropyl cellulose | 1.8 mg |
| PEG 4000 | 0.6 mg |
| Titanic dioxide | 0.6 mg |
| Coated tablet | 143.0 mg |

EXAMPLE 8

| ingredients | per tablet |
| --- | --- |
| Compound A (50 mg as free base) | 54.9 mg |
| Povidone(PVP-K30) | 38.5 mg |
| Sodium starch glycolate (Premogel) | 9.9 mg |
| Galactose | 5.3 mg |
| Hard anhydrous silicic acid | 0.7 mg |
| Magnesium stearate | 0.7 mg |
| Substances filled in a capsule | 110.0 mg |
| Empty capsule | 35.0 mg |
| Filled capsule | 255.0 mg |

EXAMPLE 9

| ingredients | per tablet |
| --- | --- |
| Compound A (50 mg as free base) | 109.8 mg |
| Povidone(PVP-K30) | 77.0 mg |
| Sodium starch glycolate (Premogel) | 19.8 mg |
| Galactose | 10.6 mg |
| Hard anhydrous silicic acid | 1.4 mg |
| Magnesium stearate | 1.4 mg |
| Substances filled in a capsule | 220.0 mg |
| Empty capsule | 35.0 mg |
| Filled capsule | 255.0 mg |

It will be understood that the specification and examples are illustrative but not limitative of the present invention and that other embodiment within the spirit and scope of the invention will suggest themselves to those skilled in the art.

What is claimed is:

1. A solid oral pharmaceutical formulation obtained according to the process comprising:

mixing, to form a resulting mixture, 2.0–10.0% by weight of dry binder cellulose, wet bind povidone or a combination thereof, 0.0–35.0% by weight of disintegrating agent starch, 2.0–20.0% by weight of co-binder saccharide and 0.0–2.0% by weight of fluid-enforcing agent with 30.0–95.0 % by weight of at least one of a pyridone carboxylic acid compound of the following formula:

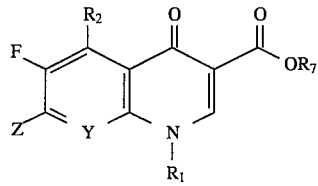

wherein $R_1$ represents a lower alkyl, a halogen-substituted lower alkyl, a lower alkenyl, a cycloalkyl or a substituted or unsubstituted-phenyl;

$R_2$ represents a hydrogen atom, a lower alkyl or an amino group;

Y represents a nitrogen atom or the group C–X in which X is a hydrogen, a halogen, or an alkoxy group;

$R_7$ represents a hydrogen or a lower alkyl group; and

Z is a group having the following formula:

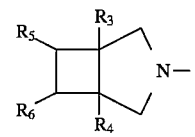

in which each of $R_3$ and $R_4$ represent independently a hydrogen or a lower alkyl group, with the proviso that one of $R_3$ and $R_4$ is a lower alkyl group; one of $R_5$ and $R_6$ is a hydrogen and another is a hydroxy, a lower alkoxy, or an amino group which is unsubstituted or substituted by a lower alkoxy or a lower alkyl group; and esters or salts thereof;

adding water to the resulting mixture to form granules; and drying, screening and mixing the granules with 0.0–3.0% by weight of lubricating agent.

2. The solid oral pharmaceutical formulation of claim 1, wherein the pyridone carboxylic acid compound is 1-cyclopropyl-6-fluoro-1,4-dihydro-4-oxo-7-([1,5,6]-amino-1-methyl-3-azabicyclo[3.2.0]heptan-3-yl)-1,8-naphtyridine-3-carboxylic acid hydrochloride.

3. A tablet formulated by compressing the pharmaceutical formulation of claim 1.

4. A capsule filled with the pharmaceutical formulation of claim 1.

* * * * *